US010408729B2

(12) United States Patent
Battefeld et al.

(10) Patent No.: US 10,408,729 B2
(45) Date of Patent: Sep. 10, 2019

(54) NEPHELOMETRIC TURBIDIMETER AND METHOD FOR CONTROLLING THE HUMIDITY OF VENTING AIR IN A NEPHELOMETRIC TURBIDIMETER

(71) Applicant: HACH LANGE GMBH, Berlin (DE)

(72) Inventors: Manfred Battefeld, Duesseldorf (DE); Hans-Joachim Kumpch, Berlin (DE); Axel Leyer, Moenchengladbach (DE); Bas De Heij, Dormagen (DE); Clemens Hanschke, Berlin (DE); Michael Kueppers, Kaarst (DE); Andreas Jonak, Meerbusch (DE); Elk Fricke, Berlin (DE); Heinz Rudde, Hueckelhoven (DE); Markus Hahn, Kempen (DE); Markus Lenhard, Viersen (DE); Rolf Uthemann, Solingen (DE); Sebastian Minke, Krefeld (DE); Andreas Golitz, Moers (DE); Bernd Gassner, Neuss (DE); Frank Steinhauer, Berlin (DE); Lothar Heidemanns, Korschenbroich (DE); Andreas Mitreiter, Kleinmachnow (DE)

(73) Assignee: HACH LANGE GMBH, Berlin (DE)

(*) Notice: Subject to any disclaimer, the term of this patent is extended or adjusted under 35 U.S.C. 154(b) by 99 days.

(21) Appl. No.: 15/527,710

(22) PCT Filed: Nov. 19, 2015

(86) PCT No.: PCT/EP2015/077151
§ 371 (c)(1),
(2) Date: May 18, 2017

(87) PCT Pub. No.: WO2016/079259
PCT Pub. Date: May 26, 2016

(65) Prior Publication Data
US 2018/0372607 A1    Dec. 27, 2018

(30) Foreign Application Priority Data

Nov. 21, 2014  (EP) .................................... 14194282

(51) Int. Cl.
*G01N 15/06*    (2006.01)
*G01N 21/15*    (2006.01)
(Continued)

(52) U.S. Cl.
CPC ............. *G01N 15/06* (2013.01); *G01N 21/15* (2013.01); *G01N 21/51* (2013.01); *G01N 21/53* (2013.01);
(Continued)

(58) Field of Classification Search
CPC .... G01N 21/4785; G01N 21/47; G01N 21/51; G01N 21/15; G01N 21/94; G01N 2021/513; G01N 2021/473
(Continued)

(56) References Cited

U.S. PATENT DOCUMENTS 4,600,416 A   7/1986 Mann
5,446,544 A   8/1995 Beers
(Continued)

FOREIGN PATENT DOCUMENTS

DE   10 2005 027 087 A1   12/2006
EP   2 487 480 A1   8/2012
(Continued)

OTHER PUBLICATIONS

C. Hostick: "Moisture Protection of Electronics", Maintenance Technology, https://www.maintenancetechnology.com/, retrieved Sep. 16, 2015, pp. 1-10 (2013).

*Primary Examiner* — Hoa Q Pham
(74) *Attorney, Agent, or Firm* — Norman B. Thot

(57) ABSTRACT

A nephelometric turbidimeter for measuring a turbidity of a liquid sample in a transparent sample cuvette. The nephelo-
(Continued)

metric turbidimeter includes a cuvette chamber housing with a cuvette chamber having the transparent sample cuvette arranged therein, and a drying apparatus. The drying apparatus includes a cuvette chamber inlet opening which vents the cuvette chamber, a cuvette chamber outlet opening which de-vents the cuvette chamber, an air circulator which circulates air from the cuvette chamber outlet opening to the cuvette chamber inlet opening, and a drying body. The drying body is provided as a container of a hygroscopic agent defined by a drying substance which is arranged in a drying path between the cuvette chamber outlet opening and the cuvette chamber inlet opening so that air flows through the drying body.

19 Claims, 2 Drawing Sheets

(51) Int. Cl.
　　*G01N 21/51*　　　(2006.01)
　　*G01N 21/53*　　　(2006.01)
(52) U.S. Cl.
　　CPC ............... *G01N 2015/0693* (2013.01); *G01N 2021/157* (2013.01); *G01N 2021/158* (2013.01); *G01N 2201/0233* (2013.01); *G01N 2201/0235* (2013.01); *G01N 2201/0238* (2013.01)

(58) Field of Classification Search
　　USPC ................... 356/335–343, 432–440, 73, 246
　　See application file for complete search history.

(56) References Cited

U.S. PATENT DOCUMENTS

| | | | |
|---|---|---|---|
| 6,016,712 A * | 1/2000 | Warden | G01N 33/4905 73/864.21 |
| 6,395,073 B1 | 5/2002 | Dauber | |
| 7,659,980 B1 * | 2/2010 | Mitchell | G01N 21/4785 356/338 |
| 9,851,297 B2 * | 12/2017 | Battefeld | G01N 21/51 |
| 2008/0155946 A1 | 7/2008 | Wang et al. | |
| 2011/0126864 A1 * | 6/2011 | Kim | A47L 15/486 134/25.2 |
| 2012/0312973 A1 | 12/2012 | D'Costa et al. | |
| 2013/0112896 A1 | 5/2013 | Dubochet et al. | |
| 2016/0109365 A1 | 4/2016 | Haase et al. | |
| 2018/0059016 A1 * | 3/2018 | Battefeld | G01N 21/51 |

FOREIGN PATENT DOCUMENTS

| | | |
|---|---|---|
| JP | 4-16745 A | 1/1992 |
| JP | 2000-111545 A | 4/2000 |
| JP | 2006-153739 A | 6/2006 |
| JP | 2006-337106 A | 12/2006 |
| KR | 100 896 044 B1 | 4/2009 |
| WO | WO 2014/183778 A1 | 11/2014 |

* cited by examiner

NEPHELOMETRIC TURBIDIMETER AND METHOD FOR CONTROLLING THE HUMIDITY OF VENTING AIR IN A NEPHELOMETRIC TURBIDIMETER

CROSS REFERENCE TO PRIOR APPLICATIONS

This application is a U.S. National Phase application under 35 U.S.C. § 371 of International Application No. PCT/EP2015/077151, filed on Nov. 19, 2015 and which claims benefit to European Patent Application No. 14194282.1, filed on Nov. 21, 2014. The International Application was published in English on May 26, 2016 as WO 2016/079259 A1 under PCT Article 21(2).

FIELD

The present invention relates to a nephelometric turbidimeter for measuring the turbidity of a liquid sample in a transparent sample cuvette.

BACKGROUND

A nephelometric turbidimeter determines the concentration of solid particles suspended in a liquid sample within a sample cuvette by projecting a measurement light beam into the liquid sample within the cuvette. An optical turbidity sensor provided outside the cuvette body detects the amount of light scattered by the suspended solid particles at an angle of typically 90° with respect to the light beam axis.

If condensate exists at the outside surface of the cuvette body, the light signal received by the measurement sensor is scattered by the condensation on the cuvette body so that the true turbidity of the liquid sample cannot be determined. The condensate at the cuvette body can also result in water drops dropping downwards from the cuvette body which causes optical and/or electronic disturbances and damage at the optics and/or electronics of the turbidimeter.

Condensation on the outside of the cuvette body and on the other parts of the turbidimeter in particular appears if the liquid sample is colder than the air in the cuvette chamber in which the cuvette is arranged during the turbidity measurement process, and if the relative humidity of the air inside the cuvette chamber is high. Condensation can be avoided by heating the cuvette chamber via a heating device which, however, results in a high consumption of electrical energy.

SUMMARY

An aspect of the present invention is to provide a nephelometric turbidimeter with an effective and simple device for avoiding condensation in the turbidimeter.

In an embodiment, the present invention provides a nephelometric turbidimeter for measuring a turbidity of a liquid sample in a transparent sample cuvette. The nephelometric turbidimeter includes a cuvette chamber housing comprising a cuvette chamber which is configured have the transparent sample cuvette be arranged therein, and a drying apparatus. The drying apparatus comprises a cuvette chamber inlet opening configured to vent the cuvette chamber, a cuvette chamber outlet opening configured to de-vent the cuvette chamber, an air circulator configured to circulate air from the cuvette chamber outlet opening to the cuvette chamber inlet opening, and a drying body. The drying body is provided as a container of a hygroscopic agent defined by a drying substance which is arranged in a drying path between the cuvette chamber outlet opening and the cuvette chamber inlet opening so that air flows through the drying body.

BRIEF DESCRIPTION OF THE DRAWINGS

The present invention is described in greater detail below on the basis of embodiments and of the drawings in which.

DETAILED DESCRIPTION

Figure 1:
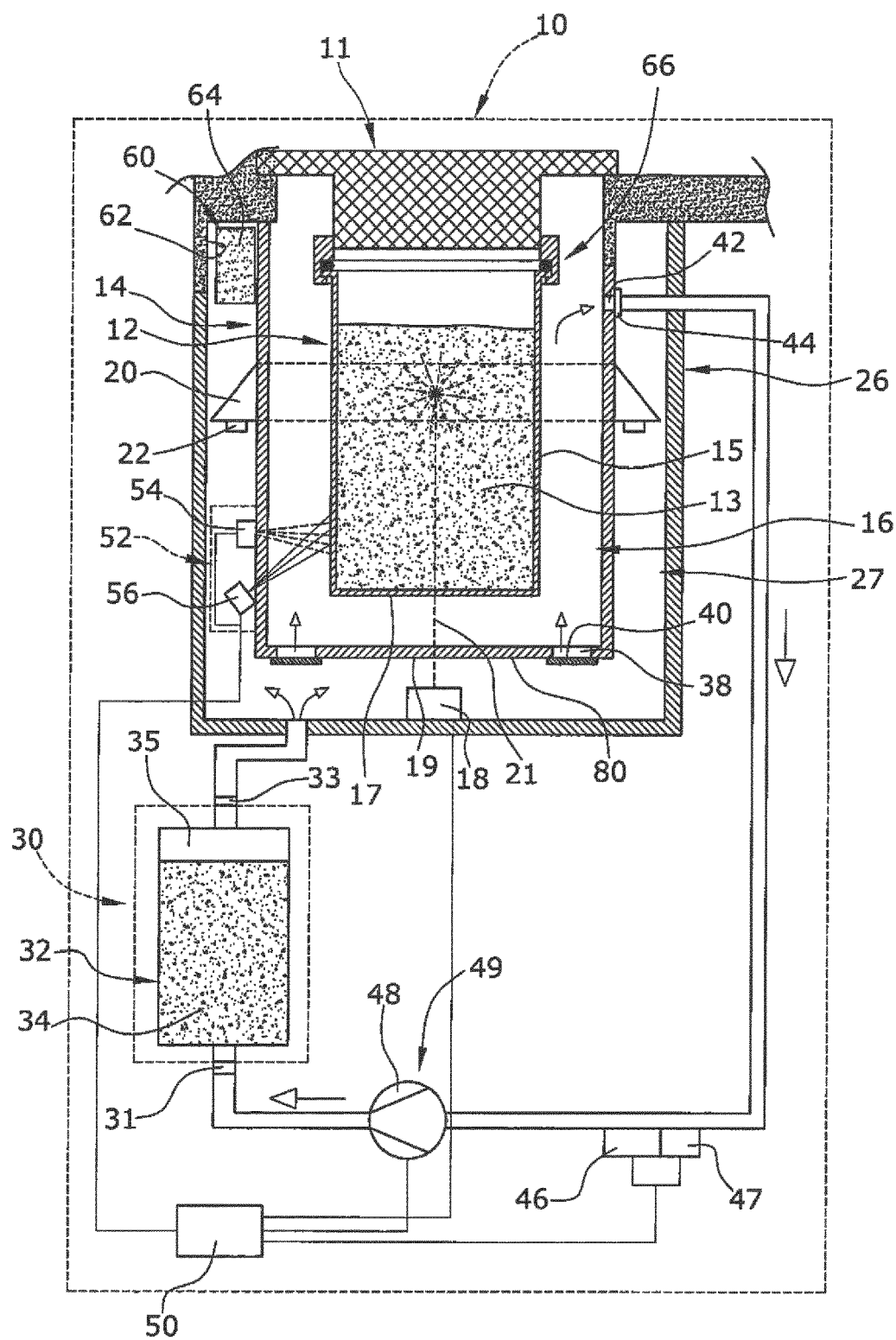
FIG. 1 schematically shows a nephelometric turbidimeter with a drying apparatus.

In an embodiment of the present invention, the nephelometric turbidimeter is provided with a transparent sample cuvette comprising the liquid sample. The sample cuvette is arranged within a cuvette chamber defined by a cuvette chamber housing. The cuvette chamber housing optically encloses the cuvette chamber to thereby shield the cuvette chamber against any environmental light within the cuvette chamber. The cuvette chamber housing also avoids a continuous exchange of air between the turbidimeter environment and the cuvette chamber.

The nephelometric turbidimeter according to the present invention can, for example, be a process device which continually exchanges the liquid sample within the sample cuvette. The sample cuvette has the approximate temperature of the water sample flowing through the sample cuvette. The sample cuvette and other parts, such as, for example, the cuvette chamber housing, can therefore have a temperature significantly below the temperature of the air within the cuvette chamber housing.

The turbidimeter is provided with a drying apparatus which comprises a fluidic cuvette chamber inlet opening for venting the cuvette chamber, and a fluidic cuvette chamber outlet opening for de-venting the cuvette chamber. The cuvette chamber inlet opening and the cuvette chamber outlet opening are connected with each other outside the cuvette chamber by a drying path. An air circulator, for example, a drying pump, is provided in the drying path to circulate or pump air from the cuvette chamber outlet opening to the cuvette chamber inlet opening. Other circulating means, such as a fan, may also be employed to circulate. A drying body for drying air is additionally arranged in the drying path between the cuvette chamber outlet opening and the cuvette chamber inlet opening. The drying body may be a container of a molecular sieve selected for its ability to bind water vapor or another hygroscopic agent.

As a result, the turbidimeter is provided with an active drying apparatus which allows continuous drying of the air in the cuvette chamber housing to a humidity level which provides that no condensation can appear within the cuvette chamber at the sample cuvette or at other parts of the turbidimeter even if the temperature difference between the liquid sample and the air within the cuvette chamber housing is relatively high. Since condensation is avoided, water drops which could cause serious problems and damage at and/or of the optics and/or the electronics are avoided.

By drying the air volume within the turbidimeter, humidity is extracted from the air; the pressure within the entire turbidimeter air volume thereby decreases. In other words, drying the air within the turbidimeter air volume causes an underpressure so that environmental air flows into the turbidimeter air volume through sealings, slits, and even through housing parts made of plastic. Only via the active and quasi-continuously working drying apparatus is it possible to continuously extract air humidity, which is continuously charged into the turbidimeter air volume. The air humidity of the turbidimeter air volume will thus be maintained at an equilibrium humidity value.

In an embodiment of the present invention, the drying apparatus can, for example, be provided with a humidity sensor which is arranged in the drying path. The humidity sensor can be a sensor for sensing the absolute humidity or the relative humidity. The humidity sensor is controlled by a control unit which also controls the air circulator or the drying pump. The humidity sensor allows for a control of the activity of the air circulator or the drying pump which thereby controls the relative or absolute humidity of the venting air to a static or to a dynamic air humidity set value.

In an embodiment of the present invention, the drying apparatus can, for example, be provided with a temperature sensor which is arranged in the drying path to sense the temperature of the venting air passing by. The temperature sensor is controlled by a control unit which also controls the air circulator or the drying pump. The temperature sensor allows for a control of the activity of the air circulator/drying pump so as to control the pumping performance depending on the air temperature. Since the absolute humidity capacity of air significantly depends on the air temperature, the pumping performance of the drying pump and/or the drying performance of the drying apparatus can be controlled depending on the air temperature. The temperature sensor also allows a rough estimation of the temperature of the liquid sample in the sample cuvette to be made if the air circulator/drying pump is stopped for some minutes so that the temperature of the air within the cuvette chamber adapts to the sample cuvette temperature. The air from the cuvette chamber is then pumped by the drying pump to the temperature sensor so that the temperature sensor detects the air temperature. This allows the temperature of the sample cuvette and the liquid sample therein to be inferred. A temperature sensor within the flowing path of the liquid sample can thus be avoided. The pumping performance can be controlled by the control unit depending on the air humidity and the air temperature if a humidity sensor is also provided.

In an embodiment of the present invention, the drying apparatus of the turbidimeter can, for example, comprise an optical condensation detector which detects condensation on the outside of the sample cuvette. The condensation detector can, for example, comprise a light source directing light to the cuvette body and a light detector which detects the light source light reflected by the cuvette body. The control unit thereby provides notice that condensation is present at the cuvette body if the reflected light is not within a defined intensity range. The condensation detector allows a more adaptive measuring and drying procedure controlled by the control unit to be realized.

If condensation is detected, no turbidity measurement is provided and the drying performance of the drying apparatus is increased until condensation is no longer detected. If a humidity sensor and/or a temperature sensor is also provided in the drying path, a dynamic air humidity set value can be calculated wherein the air humidity, the air temperature, and the condensation tendency or the condensation time after stopping the drying pump can be used to provide a rough estimate of the dew point and of the liquid sample temperature within the sample cuvette.

The cuvette chamber housing can, for example, be surrounded by an optics chamber housing which encloses an optics chamber comprising optic elements. The optics chamber housing is provided with an optics chamber inlet opening which is arranged fluidically downstream of the drying pump. The cuvette chamber and the optics chamber can, for example, be arranged fluidically in-line, and not in parallel to each other. The air can, for example, first be pumped into the optics chamber housing, and from the optics chamber housing into the cuvette chamber. By including the optics chamber into the drying circuit, the air within the optics chamber is also kept so dry that no condensation can appear at the optical elements inside the optics chamber.

In an embodiment of the present invention, the drying apparatus can, for example, comprise a disposable drying cartridge which includes the drying body. The drying cartridge is provided with a drying cartridge housing and with fluidic coupling elements which allow for a quick engagement and disengagement of the cartridge housing with or from the drying circuit of the turbidimeter.

The drying cartridge can, for example, be provided with a U-shaped cartridge housing with two substantially parallel legs and a cross portion connecting the parallel legs. An internal air inlet opening and an internal air outlet opening are provided at the end portions of the legs, respectively. One or both of the openings can be defined by an end opening of a tube leading to or from the opening to the outside of the cartridge housing. The U-shaped cartridge is compact and provides a long internal flow path. The internal tube allows for the use a long internal air flow path through the cartridge housing from one leg end portion to the other leg end portion and to provide the coupling elements for coupling the cartridge to the drying apparatus, and not at the leg end portions.

The drying body can, for example, be provided with an internal inlet opening which is arranged in a vertically low drying body portion and with an internal outlet opening which is arranged in a vertically high drying body portion. The air thereby flows through the drying body from the bottom to the top. The drying body can, for example, be a molecular sieve which may have undesirable dust particles. These dust particulates generally sink downwards due to gravity to be concentrated in the low portion of the drying body. It is therefore advantageous to minimize the discharge of dust into the drying path by directing the airflow from the bottom to the top of the drying body.

In an embodiment of the present invention, a dust filter can, for example, be provided downstream of and adjacent to the drying body. The dust filter thereby filters the dust particles coming from the drying body. The dust filter provides that no dust particulates are pumped into the cuvette chamber and/or into the optics chamber.

The drying apparatus can, for example, comprise a separate buffer drying device within a space which is fluidically connected to the cuvette chamber. The buffer drying device is a passive drying device which is not arranged in the drying path between the cuvette chamber outlet opening and the cuvette chamber inlet opening, but is arranged close to or even within the cuvette chamber and/or the optics chamber. The buffer drying device can be silica gel or any other suitable passive drying substance that is hygroscopic in nature. The buffer drying device is passive because it is not directly in the air flow path. If the active drying circuit is not working, for example, because of a defective drying pump or because of a general power loss, the passive buffer drying device can absorb humidity for at least a couple of hours or a couple of days and thereby avoid condensation and/or accumulation of water drops within the turbidimeter.

In an embodiment of the present invention, the cuvette chamber inlet opening can, for example, be closed by an inlet membrane which is permeable for air and is impermeable to liquid water. The inlet membrane allows the venting air to flow into the cuvette chamber and prevents water drops from dropping through the cuvette chamber inlet opening into the other parts of the turbidimeter.

The cuvette chamber outlet opening can, for example, be closed by an outlet membrane which is permeable for air and is impermeable for liquid water. The outlet membrane generally has the same function as the inlet membrane, i.e., preventing liquid water and water drops from running into the other parts of the turbidimeter.

In an embodiment of the present invention, the sample cuvette can, for example, be cylindrical in shape, and a measurement source can, for example, be provided to generate a measurement beam which is axially directed to the sample cuvette through a window at the bottom wall of the chamber housing to the bottom wall of the sample cuvette. The cuvette chamber inlet opening or a plurality of cuvette chamber inlet openings are provided at the chamber housing bottom wall, for example, being arranged around the window at the chamber housing bottom wall.

The method for controlling the humidity of the venting air in a nephelometric turbidimeter for measuring a turbidity of a liquid sample in a transparent sample cuvette is directed to a nephelometric turbidimeter as described above and includes a humidity sensor which is arranged in the drying path and a control unit which controls the venting air humidity. According to the method provided by the control unit, the activity of the air circulator/drying pump is continuously controlled depending on the air humidity detected by the humidity sensor to regulate the air humidity to an air humidity set value. In other words, the drying apparatus including the air circulator/drying pump is only active if the detected air humidity value is above the air humidity set value. The drying circuit is only active if necessary. The capacity of the drying body is thereby used effectively, and the energy consumption for driving the air circulator/drying pump and the wearing of the air circulator/drying pump is reduced.

The drying apparatus can, for example, comprise a temperature sensor which is arranged in the drying path. The control unit continuously controls the activity of the drying pump depending on the air humidity detected by the humidity sensor and on the air temperature detected by the temperature sensor to regulate the relative air humidity to a relative air humidity set value. The control of the relative air humidity allows for a more sophisticated control and a more efficient use of the drying resources, in particular of the capacity of the drying body.

The turbidimeter can, for example, be provided with a measurement light source which generates a measurement beam which is directed to the liquid sample within the sample cuvette. The turbidimeter is also provided with an optical turbidity sensor which receives light being scattered by the liquid sample.

The method comprises the method steps:

During the pump-stop interval: Stopping the air circulator/drying pump and periodically measuring the light intensity received by the turbidity sensor.

During the pumping interval: Starting the air circulator/drying pump and periodically measuring the light intensity received by the turbidity sensor.

Calculating the absolute air humidity set value (H) or the relative air humidity set value (RH) on the basis of the temporal course of the intensity values detected by the turbidity sensor during the time the pump was stopped and was active. The calculation can be a based on a mathematic function, but can alternatively be based on a look-up table.

The air circulator/pump circulating or pumping the liquid sample into the cuvette can, for example, be stopped during the two condensation measurement intervals.

It is assumed that the change in the light intensity received by the turbidity sensor during the first interval while the air circulator/drying pump is stopped does not result from a variation from the liquid turbidity, but can only be the result of an increasing condensation on the outside of the transparent cuvette.

During the first condensation measurement interval, when the air circulator/drying pump is stopped, a change of the signal received by the turbidity sensor is assumed to be caused by increasing condensation on the outside of the cuvette. The first interval can be of constant duration or can be stopped after a defined relative change of the light intensity received by the turbidity sensor. After the first measurement interval, the drying pump is activated and the light intensity received by the turbidity sensor is periodically detected for a defined time interval, until a defined relative change rate has been reached, or until an absolute light intensity is exceeded.

When the air circulator/drying pump is stopped at the beginning and during the first interval, the condensation at the cuvette outside increases if the temperature of the liquid sample is colder than the air in the cuvette chamber and if the dew point of the cuvette chamber air is reached during the first interval. The relative change of the intensity signal received by the turbidity sensor and the temporal course of the light intensity values therefore indicate the temperature of the liquid sample in relation to the temperature and of the humidity of fresh air in the cuvette chamber.

The condensation on the cuvette is vented-away during the second interval so that the course of the light intensity received by the turbidity sensor again indicates the temperature difference between the air and the liquid sample.

On the basis of the course of the intensity values during the first and the second interval and of the temperature of the air in the venting path, the control unit calculates a new absolute air humidity set value or a new relative air humidity set value. A set value for the absolute or relative air humidity can be determined with the apparatus and the method of the present invention without adding additional complexity to the turbidimeter.

The drying apparatus can additionally comprise an optical condensation sensor which detects condensation on the outside surface of the sample cuvette. The optical condensation sensor allows the calculation of an air humidity set value or a relative air humidity set value to in turn regulate the venting intervals with the following method steps:

Stopping the air circulator/drying pump and measuring the condensation time until the condensation sensor detects condensation at the cuvette surface after the stopping of the drying pump. As soon as condensation is detected by the condensation sensor, the air humidity is detected by the humidity sensor and the air temperature is detected by the temperature sensor. This can, for example, be realized by a short activation of the air circulator/drying pump to pump a part of the air volume from the cuvette chamber to the humidity sensor and the temperature sensor. The measured humidity value and the measured temperature is/are indicators for the temperature of the sample cuvette and the liquid sample in the sample cuvette. These values are also indicators for the grade of gas leakage of the cuvette chamber housing and therefore for the grade of humidity entry into the cuvette chamber. The control unit calculates an air humidity set value on the basis of these measurement values so that the controlled air humidity within the air volume always remains sufficiently distant from the actual dew point.

A very efficient use of the drying capacity of the drying body is thereby provided because the humidity set value is not set to an absolute minimum humidity set value, but is always adapted to the physical circumstances. The venting air is only dried as much as is necessary to avoid condensation within the cuvette chamber and/or within the optics chamber.

An embodiment of the present invention is described below with reference to the drawings.

FIG. 1 schematically shows a turbidimeter 10 for measuring the turbidity of a liquid sample 13 in a transparent and cylindrical sample cuvette 12 which is, for example, made out of glass. The present turbidimeter 10 is a so-called process device, not a so-called laboratory device, although the embodiments described herein are also applicable to high-humidity lab devices. The turbidimeter 10 is therefore provided with a sample transport arrangement comprising a sample inlet and a sample outlet at the sample cuvette 12 (which is not shown in the drawings). The liquid sample 13 is continuously or non-continuously pumped through the sample cuvette 12 to continuously or non-continuously exchange the liquid sample 13 in the sample cuvette 12.

The turbidity of a liquid is an indication of the concentration of solid particles suspended in the liquid sample 13. The turbidity is determined by projecting a measurement light beam 21 emitted by a measurement light source 18 into the liquid sample 13 and by measuring the light intensity of the light scattered by the liquid sample 13 at an angle of 90° with respect to the measurement light beam's 21 longitudinal axis within the liquid sample 13. The turbidimeter 10 is provided with a ring-like optical element 20 which is a ring-prism directing the collected scattered light to an optical turbidity sensor 22 which is circular.

The turbidimeter 10 is provided with an optically closed cuvette chamber 16 defined by a bottom wall 17 and a cup-like cuvette chamber housing 14 which includes a cuvette chamber cover 11. The cuvette chamber cover 11 holds the sample cuvette 12 releasably mounted to the cuvette chamber cover 11 via a threaded fixation ring 66. The cuvette chamber housing 14 is provided with a plane bottom wall 80 with a central optical window 19 which is transmissive for the measurement light beam 21. The plane bottom wall 80 is also provided with numerous cuvette chamber inlet openings 38 which are arranged around the central optical window 19. All cuvette chamber inlet openings 38 are covered and optically closed by an inlet membrane 40, respectively. The inlet membrane 40 can be a membrane made of black-colored PTFE, such as GORE-TEX™, and is permeable for air and impermeable for liquid water. A lateral cuvette chamber outlet opening 42 is provided through which air can flow out of the cuvette chamber 16 at the top of the cuvette chamber housing 14. The cuvette chamber outlet opening 42 is provided with an outlet membrane 44 which can be a coarse filter, but which can also be a PTFE membrane.

Outside the cuvette chamber housing 14, an optical condensation sensor 52 is provided comprising a light emitter 56 and a light detector 54, both of which are orientated to the outside surface 15 of the cylindrical portion of the sample cuvette 12. The cuvette chamber housing 14 is provided with additional light-transmissive windows corresponding to the ring-like optic element 20 and to the optical condensation sensor 52.

The cuvette chamber housing 14 is enclosed by a cup-shaped optics chamber housing 26 defining a cup-shaped optics chamber 27 between the optics chamber housing 26 and the cuvette chamber housing 14. The measurement light source 18, the ring-like optic element 20, the optical turbidity sensor 22, and the optical condensation sensor 52 are arranged within the optics chamber 27. A passive drying device 60 is arranged in an upper portion 62 of the optics chamber 27. The passive drying device 60 is defined by several cushions of silica gel as a drying substance 64.

The drying path between the cuvette chamber outlet opening 42 and an optics chamber inlet opening 28 of the optics chamber housing 26 comprises an air circulator 49 which is a drying pump 48 in the shown embodiment, e.g., a membrane pump, and a drying cartridge 30 comprising a drying body 32 defined by a drying substance 34 which is a molecular sieve. The drying path also comprises a humidity sensor 46 and a temperature sensor 47 which can be realized as one single sensor array. The turbidimeter 10 is provided with a control unit 50 which electronically and electrically controls the humidity sensor 46, the temperature sensor 47, the drying pump 48, the measurement light source 18, the optical condensation sensor 52, and the optical turbidity sensor 22.

Figure 2:
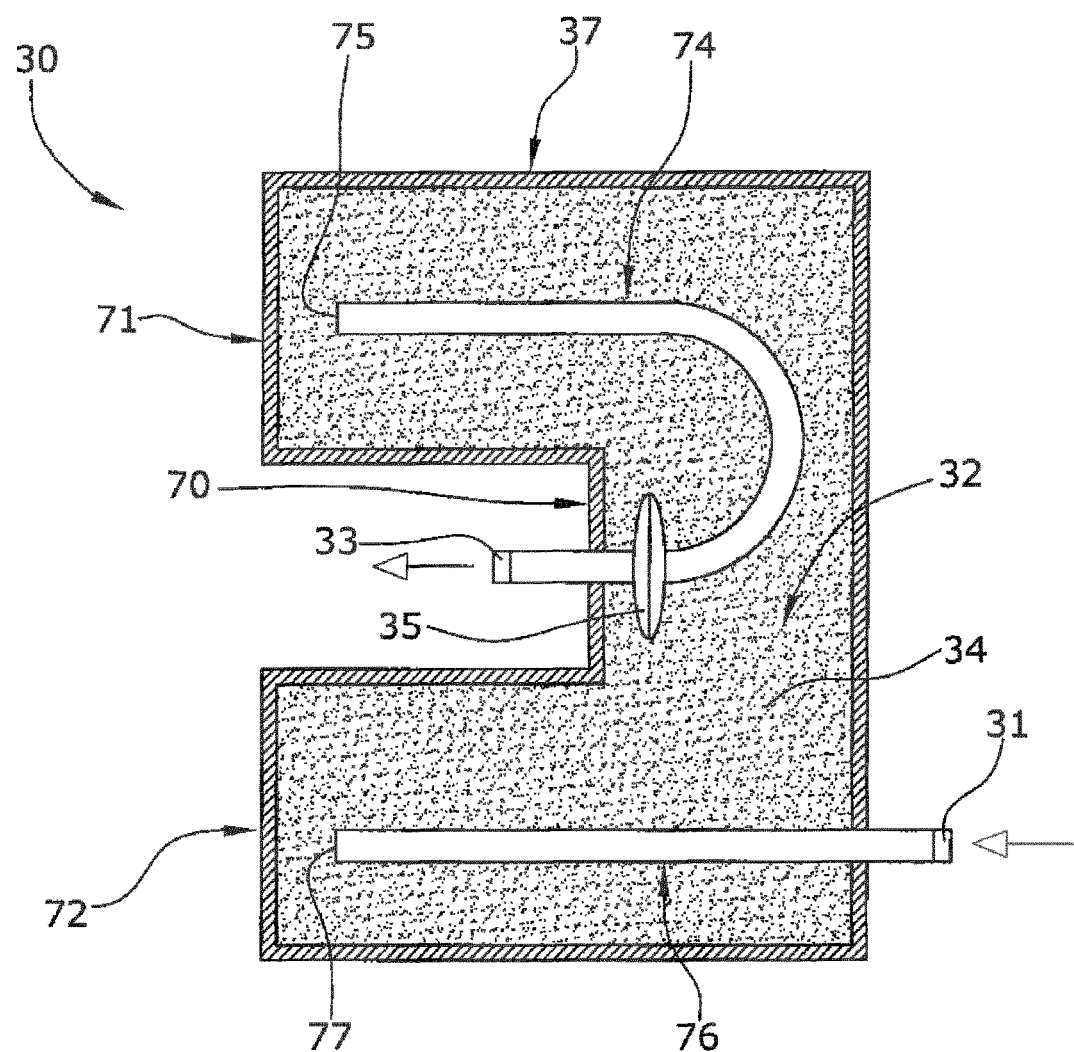
FIG. 2 shows a drying body provided as a drying cartridge of the turbidimeter of FIG. 1.

The drying cartridge 30 is shown in more detail in FIG. 2. The drying cartridge 30 is provided with a U-shaped cartridge housing 37 defining two substantially parallel legs 71, 72 and a cross portion 70 connecting the legs 71, 72. The cartridge housing legs 71, 72 lie in a horizontal plane, whereas the cross portion 70 is orientated vertically. The drying cartridge 30 also comprises an inlet tube 76 with an internal inlet opening 77 at the end portion of the bottom leg 72 and with a coupling element 31 outside the cartridge housing 37. The drying cartridge 30 also comprises an outlet tube 74 with an internal inlet opening 75 at the end portion of the top leg 71 and with a coupling element 33 outside the cartridge housing 37. The outlet tube 74 is also provided with a dust filter 35.

The control unit 50 is provided with an electronic memory wherein a humidity set value H and/or a relative humidity set value RH is stored. The control unit 50 controls the activity of the drying pump 48 dependent on the humidity value h and the temperature value t detected by the humidity sensor 46 and the temperature sensor 47 to keep the humidity at the respective set value H,RH. The control unit 50 periodically stops the humidity control to perform a calibration cycle. The calibration cycle starts with the stopping of the drying pump 48 so that the temperature of the air inside the cuvette chamber 16 is adapted to the temperature of the liquid sample 13. If, before the temperature adaption, the liquid sample 13 is much colder than the air in the cuvette chamber 16, condensation at the outside surface 15 of the sample cuvette 12 will appear after a while. The optical condensation sensor 52 detects the condensation and the condensation detection is registered by the control unit 50. The time t between the stopping of the drying pump 48 and the detection of condensation is the condensation duration d. The control unit 50 now activates the drying pump 48 to pump a small air volume from the cuvette chamber 16 to the humidity sensor 46 and the temperature sensor 47 to immediately determine the humidity h and the temperature t of this air volume. The control unit 50 then calculates a new air humidity set value H or relative air humidity set value RH on the basis of the condensation duration, the air temperature t, and the air humidity h just measured. The calculation of the new set values can be based on a mathematic function or can be based on the use of a look-up table.

The control unit 50 then continues to control the air humidity or the relative air humidity on the basis of the new set value H, RH.

The present invention is not limited to embodiments described herein; reference should be had to the appended claims.

What is claimed is:

1. A nephelometric turbidimeter for measuring a turbidity of a liquid sample in a transparent sample cuvette, the nephelometric turbidimeter comprising:
   a cuvette chamber housing comprising a cuvette chamber which is configured have the transparent sample cuvette be arranged therein; and
   a drying apparatus comprising:
      a cuvette chamber inlet opening configured to vent the cuvette chamber,
      a cuvette chamber outlet opening configured to de-vent the cuvette chamber,
      an air circulator configured to circulate air from the cuvette chamber outlet opening to the cuvette chamber inlet opening, and
      a drying body which is provided as a container of a hygroscopic agent defined by a drying substance which is arranged in a drying path between the cuvette chamber outlet opening and the cuvette chamber inlet opening so that air flows through the drying body.

2. The nephelometric turbidimeter as recited in claim 1, wherein the drying apparatus further comprises a humidity sensor which is arranged in the drying path.

3. The nephelometric turbidimeter as recited in claim 1, wherein the drying apparatus further comprises a temperature sensor which is arranged at the drying path.

4. The nephelometric turbidimeter as recited in claim 1, wherein,
   the transparent sample cuvette comprises an outside surface, and
   the drying apparatus further comprises an optical condensation detector which is configured to detect a condensation on the outside surface of the transparent sample cuvette.

5. The nephelometric turbidimeter as recited in claim 1, wherein the air circulator is a drying pump, and
   further comprising:
      an optics chamber housing which is configured to surround the cuvette chamber housing and to enclose an optics chamber comprising optic elements, the optics chamber housing comprising an optics chamber inlet opening which is arranged fluidically downstream of the drying pump.

6. The nephelometric turbidimeter as recited in claim 5, further comprising:
   a dust filter arranged downstream of the drying body and upstream of at least one of the cuvette chamber and the optics chamber.

7. The nephelometric turbidimeter as recited in claim 1, wherein the drying apparatus further comprises a disposable drying cartridge in which the drying body is arranged, the disposable drying cartridge comprising a cartridge housing and fluidic coupling elements.

8. The nephelometric turbidimeter as recited in claim 7, wherein the disposable drying cartridge further comprises:
   a U-shaped cartridge housing which comprise a first leg and a second leg which are configured to be substantially parallel with each other;
   a cross portion which connects the first leg with the second leg; and
   an internal inlet opening and an internal outlet opening arranged at respective end portions of the first leg and the second leg, at least one of the internal outlet opening and the internal inlet opening being provided as an opening of a tube which is arranged to lead to an outside of the U-shaped cartridge housing.

9. The nephelometric turbidimeter as recited in claim 8, wherein the drying body comprises the internal inlet opening arranged in a low drying body portion and the internal outlet opening arranged in a high drying body portion.

10. The nephelometric turbidimeter as recited in claim 1, wherein the drying apparatus further comprises a separate buffer dryer arranged within a space which is fluidically connected to the cuvette chamber.

11. The nephelometric turbidimeter as recited in claim 1, further comprising:
    an inlet membrane which is configured to be permeable for air, impermeable for water, and to close the cuvette chamber inlet opening.

12. The nephelometric turbidimeter as recited in claim 1, further comprising:
    an outlet membrane which is configured to be permeable for air, impermeable for water, and to close the cuvette chamber outlet opening.

13. The nephelometric turbidimeter as recited in claim 1, wherein,
    the transparent sample cuvette is configured to be cylindrical and to further comprise a sample cuvette bottom wall,
    the cuvette chamber housing comprises a cuvette chamber housing bottom wall, and
    the cuvette chamber inlet opening is arranged at the cuvette chamber housing bottom wall, and
    further comprising:
    a window arranged at the cuvette chamber housing bottom wall; and
    a measurement light source which is configured to generate a measurement beam directed to the transparent sample cuvette axially through the window and through the sample cuvette bottom wall.

14. The nephelometric turbidimeter as recited in claim 1, wherein the air circulator is a drying pump.

15. The nephelometric turbidimeter as recited in claim 1, wherein the air circulator is an electric fan.

16. A method for controlling a venting air humidity in a nephelometric turbidimeter for measuring a turbidity of a liquid sample in a transparent sample cuvette, the method comprising:
    providing the nephelometric turbidimeter comprising:
       a cuvette chamber housing comprising a closed cuvette chamber which is configured have the transparent sample cuvette be arranged therein; and
       a drying apparatus comprising:
          a cuvette chamber inlet opening configured to vent the closed cuvette chamber,
          a cuvette chamber outlet opening configured to de-vent the closed cuvette chamber,
          an air circulator configured to circulate air from the cuvette chamber outlet opening to the cuvette chamber inlet opening,
          a drying body arranged in a drying path between the cuvette chamber outlet opening and the cuvette chamber inlet opening so that air flows through the drying body,
          a system humidity sensor arranged at the drying path, and a control unit configured to control the venting air humidity; and via the control unit, continuously controlling an activity of the air circulator dependent on an air humidity detected by the system humidity sensor so as to regulate the venting air humidity to an air humidity set value.

17. The method as recited in claim 16, wherein, the drying apparatus further comprises a temperature sensor arranged in a venting path, the temperature sensor being configured to detect an air temperature, and the system humidity sensor is configured to detect the air humidity, and the method further comprises:

via the control unit, continuously controlling an activity of the air circulator dependent on the air humidity detected by the system humidity sensor and on the air temperature detected by the temperature sensor so as to regulate a relative air humidity to a relative air humidity set value.

18. The method as recited in claim 17, wherein, the nephelometric turbidimeter further comprises,
- a measurement beam source which is configured to generate a measurement beam directed to the transparent sample cuvette, and
- a turbidity sensor arranged outside the transparent sample cuvette, the turbidity sensor being configured to detect light which is scattered by the liquid sample, and the control unit is further configured to determine the air humidity set value by:

stopping the air circulator;

periodically measuring a light intensity received by the turbidity sensor;

starting the air circulator;

periodically measuring the light intensity received by the turbidity sensor; and calculating an absolute air humidity set value or the relative air humidity set value on the basis of a temporal course of a light intensity value detected by the turbidity sensor when the air circulator was stopped and was active.

19. The method as recited in claim 17, wherein the drying apparatus further comprises an optical condensation sensor which is configured to detect a condensation on an outside surface of the transparent sample cuvette, and the control unit is further configured to determine the air humidity set value by:

stopping the air circulator;

measuring a condensation duration until the optical condensation sensor detects a condensation at the outside surface of the transparent sample cuvette;

measuring the air humidity detected by the system humidity sensor;

measuring the air temperature detected by the temperature sensor; and calculating an absolute air humidity set value or the relative air humidity set value on the basis of the condensation duration, the air temperature, and the air humidity.

* * * * *